United States Patent [19]

Kinney

[11] Plant 4,263

[45] June 13, 1978

[54] PEAR TREE

[76] Inventor: Charles Lyle Kinney, 1356 Siskiyou, Medford, Oreg. 97501

[21] Appl. No.: 817,101

[22] Filed: Jul. 19, 1977

[51] Int. Cl.[2] ..... A01H 5/03

[52] U.S. Cl. ..... Plt./36

[58] Field of Search ..... Plt./36

*Primary Examiner*—Robert E. Bagwill

*Attorney, Agent, or Firm*—Kolisch, Hartwell, Dickinson & Stuart

[57] ABSTRACT

A novel pear variety originating as a sport of Regal Red Comice, characterized by its solid red fruit color, Comice shape and smaller tree habit.

2 Drawing Figures

1

This invention relates to a new and unique variety of pear tree. The pear tree originated as a sport of the variety referred to as Regal Red Comice, U.S. Plant Pat. No. 2,527, issued June 1, 1965.

The present discovery originated as a sport thrown by a Regal Red Comice pear tree in a cultivated orchard on property owned by the inventor Charles Lyle Kinney. The property is located on Pioneer Road about one and one-half miles southwest of the city of Phoenix, Jackson County, in the State of Ore.

The parent variety, Regal Red Comice which is the subject of U.S. Plant Pat. No. 2,527, is characterized by thick trunks and limbs having a reddish-brown bark. It is a tree of vigorous growth, very upright, having pinkish-white blossoms. The ripe fruit of the parent variety has an overall reddish skin having a slight purplish tint and, as has become more prevalent through the years, having yellow stripes running from calyx to stem. The parent variety also has pronounced elongate shape.

The new variety is not as vigorous as the parent, being more a spur type. It is a smaller tree and grows more slowly. The fruit is a solid red throughout the growing season and has no purplish tint. The coloration of the new variety generally is unaffected by the degree of exposure of the fruit to the sun.

The new variety has no yellow stripes as does the parent, Regal Red Comice. It is shaped like the usual Comice variety, rather than having the elongate shape of the parent Regal Red Comice variety. The new variety fruit has a very slight yellowish undercoat when ripe, whereas the Regal Red Comice parent has a mottled greenish-yellow undercoat when ripe.

The ripening time of the new variety is from 6 to 8 days later than the parent variety.

Asexual reproduction was performed by the inventor by grafting and budding. The grafting and budding illustrated that the distinctive characteristics mentioned herein were established and transmitted through succeeding propagations.

Accompanying this specification are two color photographs.

Figure 1:
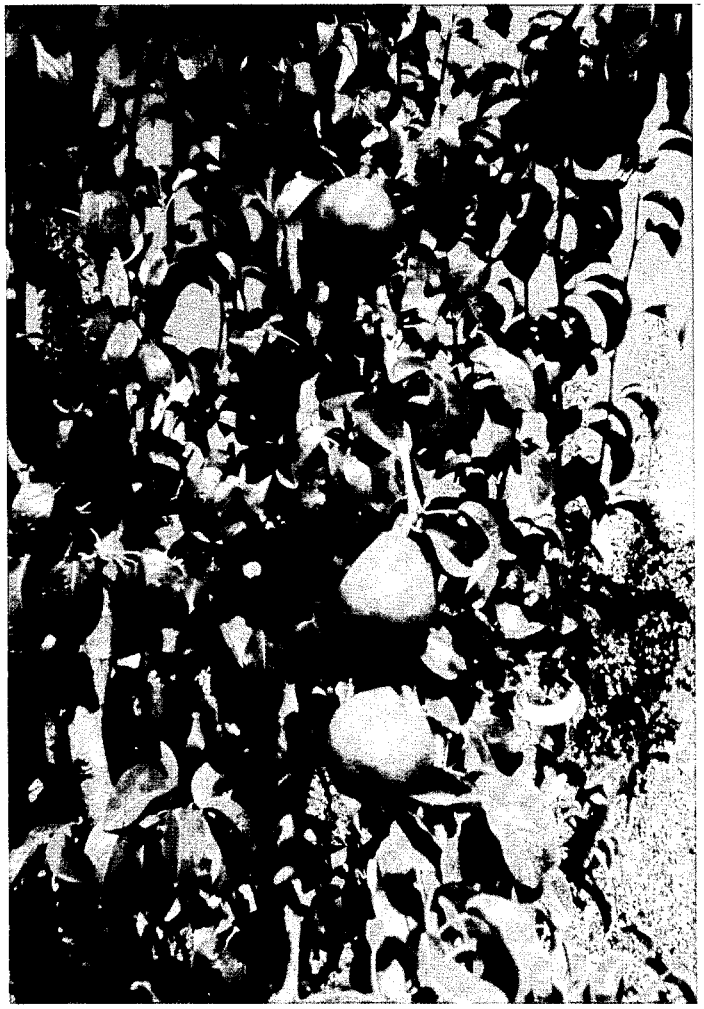
FIG. 1 is a photograph showing the new pear on the tree.
Figure 2:
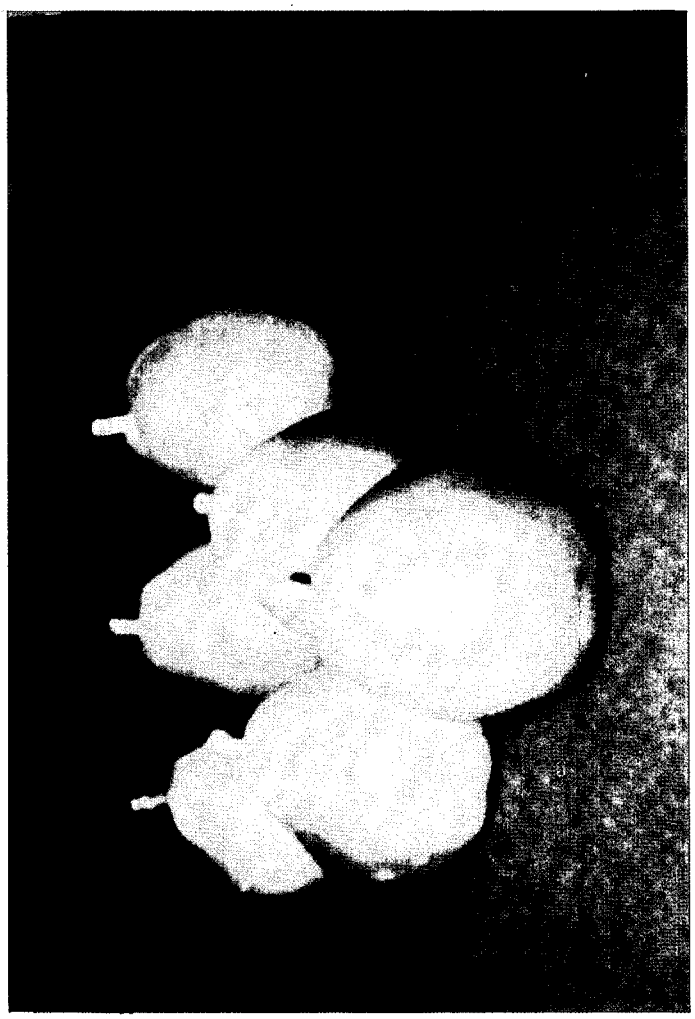
FIG. 2 shows a group of the new pears.

There follows a detailed description of the new variety of pear tree, such description being based upon observations of pear specimens grown upon the inventor's property described above. The color terminology

2 is in accordance with the "Munsell Book of Color" (abridged edition), 1929–1942.

Tree: Slow growth, hardy, non-vigorous, regular bearing.

*Trunk.*—Stocky and smooth.

*Branches.*—Brown, substantially smooth, medium thickness.

*Leaves.*—Substantially identical to parent variety, Regal Red Comice; medium length, width and size, ovate, taper-pointed, dark green and smooth. Margins are finely serrated with the petiole being medium length and thickness.

*Flowers.*—Substantially identical to the parent variety, Regal Red Comice; date of bloom — 4 to 15 days approximately, late, medium in size, light red to pink or white when mature, and fertile.

Fruit: Similar in shape to standard Comice variety, large substantially uniform shape with sides substantially equal; roundish shape; date of ripening — approximately September 22. Hangs well.

*Skin.*—Thick; smooth; glossy.

*Flesh.*—White; fine, tender, juicy, sweet.

*Stem.*—Short and thick.

*Core.*—Medium; axile.

*Calyx.*—Small and open.

*Basin.*—Deep, wide, symmetrical and smooth.

*Calyx Tube.*—Medium length and conical.

*Keeping Quality.*—Good to January 15.

*Color.*—Substantially solid red throughout the growing season, brightening and lighter when ripe, but having little or no purplish tint, and having a very slight yellowish undercoat when ripe. The red color is between red hue 5.0 R, value 4, chroma 8-10 and red hue 5.0 R, value 3, chroma 8-10 in the "Munsell Book of Color" referred to above.

What is claimed is:

1. A new and distinct variety of pear tree, substantially as shown and described herein, distinguished principally from its parent, the Regal Red Comice, by being a spur-type tree bearing fruit, having a substantially solid red color throughout the growing season, with little or no purplish tint and having very slight yellowish undercoat when ripe, having substantially thicker and tougher skin, and having a rounded shape more nearly similar to the standard Doyenné Du Comice.

* * * * *